United States Patent
Hyun et al.

(10) Patent No.: US 9,186,062 B2
(45) Date of Patent: Nov. 17, 2015

(54) SYSTEM AND METHOD FOR PROVIDING 2-DIMENSIONAL COMPUTERIZED-TOMOGRAPHY IMAGE CORRESPONDING TO 2-DIMENSIONAL ULTRASOUND IMAGE

(71) Applicants: SAMSUNG MEDISON CO. LTD., Hongchun-gun, Kangwon-do (KR); Korea Advanced Institute of Science and Technology, Daejeon (KR)

(72) Inventors: Dong-Gyu Hyun, Seoul (KR); Jong-Beom Ra, Daejeon (KR); Duhgoon Lee, Daejeon (KR); Woo Hyun Nam, Busan (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 171 days.

(21) Appl. No.: 13/867,799

(22) Filed: Apr. 22, 2013

(65) Prior Publication Data
US 2013/0231559 A1   Sep. 5, 2013

Related U.S. Application Data

(62) Division of application No. 12/848,024, filed on Jul. 30, 2010, now Pat. No. 8,447,383.

(30) Foreign Application Priority Data

Aug. 3, 2009   (KR) .................. 10-2009-0071351

(51) Int. Cl.
*A61B 5/00* (2006.01)
*A61B 8/13* (2006.01)
(Continued)

(52) U.S. Cl.
CPC .............. *A61B 5/0035* (2013.01); *A61B 6/032* (2013.01); *A61B 8/13* (2013.01); *G06T 7/0038* (2013.01); *G06T 2207/30004* (2013.01)

(58) Field of Classification Search
CPC ........ A61B 8/13; A61B 6/032; A61B 5/0035; G06T 7/0038; G06T 2207/30004
See application file for complete search history.

(56) References Cited

U.S. PATENT DOCUMENTS 5,538,004 A * 7/1996 Bamber ........................ 600/443
5,640,956 A    6/1997 Getzinger et al.
(Continued)

FOREIGN PATENT DOCUMENTS

JP   2007319676 A   12/2007
JP   2008-086400 A   4/2008
(Continued)

OTHER PUBLICATIONS

Birkfellner et al., "Rigid 2D/3D slice-to-volume registration and its application on fluoroscopic CT images", Medical Physics, 34, 246-255, 2007.*
Wikipedia "Image segmentation", archived Jul. 7, 2009, retrieved Nov. 5, 2014 from <http://en.wikipedia.org/w/index.php?title=Image_segmentation&oldid=300814470>.*
Japanese Office Action issued in Japanese Application No. 2010-172675 dated Mar. 18, 2014, w/English translation.
Korean Office Action issued in Korean Patent Application No. 10-2009-0071351, dated Sep. 27, 2011.
Korean Notice of Allowance issued in Korean Patent Application No. 10-2009-0071351, dated Feb. 3, 2012.
(Continued)

*Primary Examiner* — Long V Le
*Assistant Examiner* — Colin T Sakamoto
(74) *Attorney, Agent, or Firm* — McDermott Will & Emery LLP

(57) ABSTRACT

Embodiments for providing a 2-dimensional (D) computerized-tomography (CT) image corresponding to a 2-D ultrasound image through image registration between 3-D ultrasound and CT images are disclosed. An imaging system comprises a CT imaging unit, an ultrasound image forming unit, a storing unit, a processor and a display unit. The processor extracts the 2-D CT image from the 3-D ultrasound-CT registered image by performing a rigid-body transform upon the 3-D ultrasound image and calculating similarities between reference images and the 2-D ultrasound images, wherein the reference images are obtained through the rigid-body transform.

10 Claims, 5 Drawing Sheets

(51) Int. Cl.
*A61B 6/03* (2006.01)
*G06T 7/00* (2006.01)

(56) References Cited

U.S. PATENT DOCUMENTS

| | | |
|---|---|---|
| 2007/0280556 A1 | 12/2007 | Mullick et al. |
| 2008/0137927 A1 | 6/2008 | Altmann et al. |
| 2009/0080742 A1 | 3/2009 | Moriya |
| 2009/0093717 A1 | 4/2009 | Carneiro et al. |

FOREIGN PATENT DOCUMENTS

| | | |
|---|---|---|
| JP | 2008188193 A | 8/2008 |
| JP | 2008264520 A | 11/2008 |
| JP | 2009072432 A | 4/2009 |
| JP | 2009112468 A | 5/2009 |
| JP | 2009-291618 A | 12/2009 |
| KR | 10-2008-0053057 A | 6/2008 |
| KR | 10-2008-0053224 | 6/2008 |
| WO | 2008021245 A2 | 2/2008 |

OTHER PUBLICATIONS

Huang et al. "Dynamic 2D Ultrasound and 3D CT Image Registration of the Beating Heart," IEEE Transactions on Medical Imaging, vol. 28, No. 8, pp. 1179-1189, 2009.

Nam et al. "Anatomical feature extraction in 3D B-mode ultrasound liver images for CT-ultrasound image registration," Int J CARS, vol. 3 (Suppl1), pp. S401-S402, 2008.

Porter et al. "Three Dimensional Frameless Fusion of Ultrasound Liver Volumes," 1999 IEEE Ultrasonics Symposium, pp. 1577-1580.

Extended European Search Report or EP 10170225-6-2218, 6 pages, mailed Oct. 26, 2010.

Bortfeld et al., Effects of intra-fraction motion on IMRT dose delivery; statistical analysis and simulation, Phys. Med. Biol. 47, pp. 2203-2220 (2002).

Pitiot et al., "Piecewise Affine Registration of Biological Images for Volume Reconstruction," Medical Image Analysis, Elsevier, 19 pages (Received Aug. 9, 2004).

\* cited by examiner

SYSTEM AND METHOD FOR PROVIDING 2-DIMENSIONAL COMPUTERIZED-TOMOGRAPHY IMAGE CORRESPONDING TO 2-DIMENSIONAL ULTRASOUND IMAGE

CROSS-REFERENCE TO RELATED APPLICATIONS

This application is a Divisional of U.S. application Ser. No. 12/848,024, filed Jul. 30, 2010, and claims benefit of priority to Korean Patent Application No. 10-2009-0071351 filed on Aug. 3, 2009, the entire contents of each are hereby incorporated by reference.

TECHNICAL FIELD

The present disclosure generally relates to ultrasound imaging, and more particularly to a system and method for providing a 2-dimensional (D) computerized-tomography (CT) image corresponding to a 2-D ultrasound image through image registration between 3-D ultrasound and CT images of a target object.

BACKGROUND

An ultrasound diagnostic system has been extensively used in the medical field due to its non-invasive and non-destructive nature. The ultrasound diagnostic system can provide an ultrasound image of the inside of a target object in real-time without resorting to any incisions. However, the ultrasound diagnostic system suffers from inherent shortcomings of an ultrasound image such as a low signal-to-noise ratio and a limited field of view. Thus, an image registration between a CT image and an ultrasound image has been introduced to compensate for inherent deficiencies of the ultrasound image.

Generally, an image registration between a CT image and an ultrasound image is performed by means of a spatial sensor. Errors may occur during the image registration due to spatial movement variation in the inner part of a target object such as respiration. If an ultrasound probe is moved and a 2-D ultrasound image is newly obtained, then the spatial sensor is typically used to determine whether or not the newly obtained 2-D ultrasound image exists in a pre-obtained 3-D ultrasound image, and to extract a 2-D CT image corresponding to the newly obtained 2-D ultrasound image from a 3-D ultrasound-CT registered image.

SUMMARY

There are disclosed embodiments for providing a 2-D CT image corresponding to a 2-D ultrasound image through an image registration between 3-D ultrasound and CT images of a target object, independent of a spatial sensor. In an exemplary embodiment, by way of non-limiting example, an image system comprises: a computerized-tomography (CT) imaging unit configured to form a 3-dimensional (D) CT image of a target object; an ultrasound image forming unit configured to form 3- and 2-D ultrasound images of the target object; a storing unit configured to store sets of transform parameters for use in performing a rigid-body transform upon the 3-D ultrasound image; a processor configured to perform an image registration between the 3-D ultrasound and CT images, establish a 3-D coordinate system with a reference surface being set thereon in the 3-D ultrasound image, perform the rigid-body transform upon the 3-D ultrasound image by sequentially applying the sets of transformation parameters retrieved from the storing unit, calculate similarities between reference images corresponding to the reference surface and the 2-D ultrasound image, and extract a 2-D CT image corresponding to the 2-D ultrasound image from the 3-D ultrasound-CT registered image based on the calculated similarities; and a display unit configured to display the 2-D ultrasound image and the resultant 2-D CT image, wherein each of the reference images is obtained at every rigid-body transform when the sets of transformation parameters are sequentially applied thereto and the 2-D ultrasound image is related to a region of interest (ROI) of the target object.

In another embodiment, a method of imaging comprises: forming 3-D ultrasound and CT images of a target object; performing an image registration between the 3-D ultrasound and CT images to form a 3-D ultrasound-CT registered image; forming a 2-D ultrasound image related to a region of interest (ROI) of the target object; establishing a 3-D coordinate system with a reference surface being set thereon in the 3-D ultrasound image; performing a rigid-body transform upon the 3-D ultrasound image by sequentially applying sets of transform parameters and calculating similarities between reference surface images and the 2-D ultrasound image, wherein each of the reference surface images is obtained every rigid-body transform when the sets of transform parameters are sequentially applied thereto and each of the reference surface images corresponds to the reference surface; extracting a 2-D CT image corresponding to the 2-D ultrasound image from the 3-D ultrasound-CT registered image based on the calculated similarities; and displaying the 2-D ultrasound and CT images.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
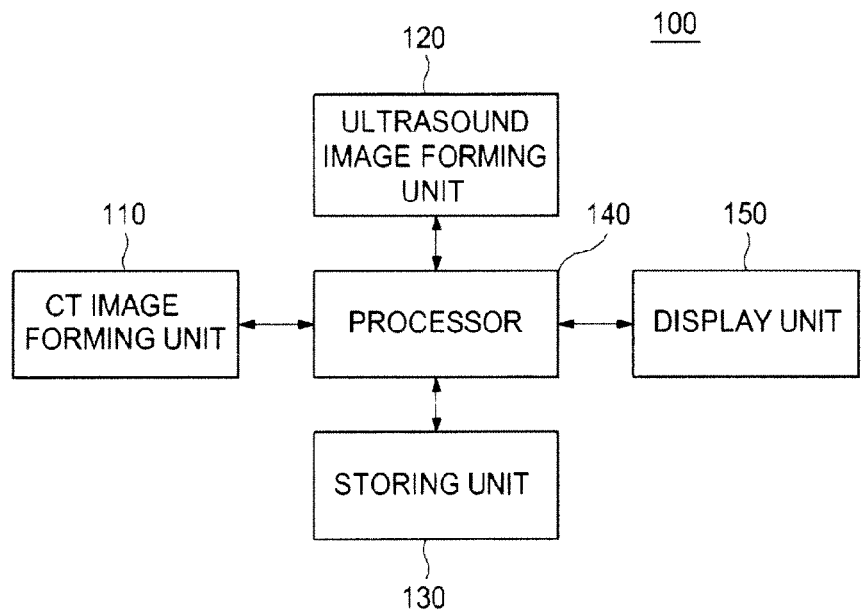
FIG. 1 is an embodiment illustrating a schematic diagram of an ultrasound imaging system in accordance with the present disclosure.

Referring to FIG. 1, there is shown an embodiment illustrating a schematic diagram of an ultrasound imaging system 100 in accordance with the present disclosure. In an exemplary embodiment, the ultrasound imaging system 100 may comprise a computerized-tomography (CT) image forming unit 110, an ultrasound image forming unit 120, a storing unit 130, a processor 140 and a display unit 150. The ultrasound imaging system 100 may further comprise a user input unit (not shown) configured to receive input data from a user.

The CT image forming unit 110 may be configured to form a 3-D CT image of a target object (e.g., a liver). It is noted that the formation of the 3-D CT image may be accomplished by using techniques well known in the art. The 3-D CT image may be comprised of a plurality of 2-D CT images of the target object. The 3-D CT image of the target object is then sent to the processor 140.

The ultrasound image forming unit 120 may be configured to form 3- and 2-D ultrasound images of the target object. In particular, the ultrasound image forming unit 120 may be operable to transmit ultrasound signals to the target object and receive reflected ultrasound signals (i.e., ultrasound echo signals) therefrom to form the 3-D ultrasound image of the target object. Also, the ultrasound image forming unit 120 may be operable to transmit ultrasound signals to the target object and receive reflected ultrasound echo signals therefrom to form the 2-D ultrasound image with respect to a region of interest (ROI) of the target object.

Figure 2:
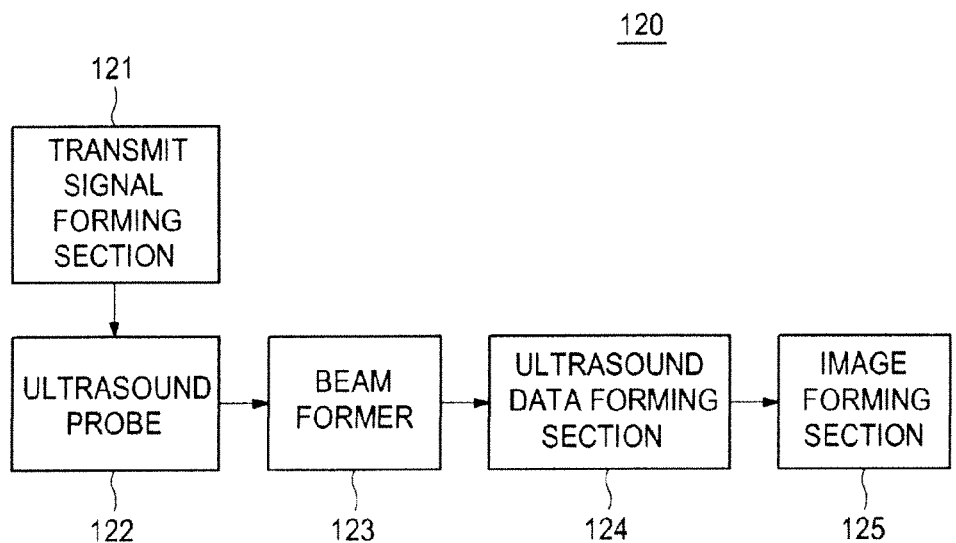
FIG. 2 is an embodiment illustrating a schematic diagram of an ultrasound image forming unit in accordance with the present disclosure.

Referring to FIG. 2, there is shown an embodiment illustrating a schematic diagram of the ultrasound image forming unit 120 in accordance with the present disclosure. In an exemplary embodiment, the ultrasound image forming unit 120 may include a transmit signal forming section 121, an ultrasound probe 122 having a multiplicity of transducer elements (not shown), a beam former 123, an ultrasound data forming section 124 and an image forming section 125.

The transmit signal forming section 121 may be configured to form first electrical transmit signals to obtain a plurality of image frames for use in imaging the 3-D ultrasound image in consideration of positions and focusing points of the transducer elements in the ultrasound probe 122. Also, the transmit signal forming section 121 may be configured to form second electrical transmit signals to obtain an image frame for use in imaging the 2-D ultrasound image in consideration of the positions and focusing points of the transducer elements. For example, the image frame may include a brightness (B)-mode image. Herein, the first and second electrical transmit signals may be selectively formed in response to input data from a user. The first and second electrical transmit signals are transmitted to the ultrasound probe 122.

In response to the first electrical transmit signals from the transmit signal forming section 121, the ultrasound probe 122 may be configured to generate and transmit ultrasound signals to the target object and then receive ultrasound echo signals reflected therefrom to form first electrical receive signals. Also, in response to the second electrical transmit signals from the transmit signal forming section 121, the ultrasound probe 122 may be configured to generate and transmit ultrasound signals to the target object and then receive ultrasound echo signals reflected therefrom to form second electrical receive signals. The first and second electrical receive signals are sent to the beam former 123.

The beam former 123 may be configured to receive the first electrical receive signals from the ultrasound probe 122 and convert them from analog to digital to form first digital signals. Thereafter, the beam former 123 may be operable to receive-focus the first digital signals in consideration of the positions and focusing points of the transducer elements to thereby form first receive-focus signals. Also, the beam former 123 may be configured to receive the second electrical receive signals from the ultrasound probe 122 and convert them from analog to digital to form second digital signals. Then, the beam former 123 may be operable to receive-focus the second digital signals in consideration of the positions and focusing points of the transducer elements to thereby form second receive-focus signals. The first and second receive-focus signals are sent to the ultrasound data forming section 124.

The ultrasound data forming section 124 may be configured to receive the first receive-focus signals from the beam former 123 and form first ultrasound data based on the first receive-focus signals received. Also, the ultrasound data forming section 124 may be configured to receive the second receive-focus signals from the beam former 123 and form second ultrasound data based on the second receive-focus signals received. In an exemplary embodiment, the ultrasound data forming section 124 may be configured to perform various signal processes (e.g., a gain adjustment, filtering and so on) upon the first and second receive-focus signals in order to form the first and second ultrasound data. The first and second ultrasound data are sent to the image forming section 125.

The image forming section 125 may be configured to receive the first ultrasound data from the ultrasound data forming section 124 and form a 3-D ultrasound image of the target object based on the received first ultrasound data. Also, the image forming section 125 may be configured to receive the second ultrasound data from the ultrasound data forming section 124 and form a 2-D ultrasound image with respect to the ROI of the target object based on the received second ultrasound data. The 3-D and 2-D ultrasound images are sent to the processor 140.

Referring back to FIG. 1, the storing unit 130 may be configured to store transform parameters for use in translating and rotating the 3-D ultrasound image of the target object. In an exemplary embodiment, the storing unit 130 may be operable to store sets of transform parameters (as shown below in Table 1, but not limited thereto) for performing a rigid-body transform upon the 3-D ultrasound image of the target object. Herein, x, y and z may represent width, height and depth axes, respectively, at the 3-D ultrasound image. Further, $\theta_x$, $\theta_y$ and $\theta_z$ may denote rotation components centering on the respective width, height and depth axes.

TABLE 1

Sets of Transform Parameters
$(x, y, z, \theta_x, \theta_y, \theta_z)$ $x_0, y_0, z_0, \theta_{x0}, \theta_{y0}, \theta_{z0}$
$x_1, y_0, z_0, \theta_{x0}, \theta_{y0}, \theta_{z0}$
$x_2, y_0, z_0, \theta_{x0}, \theta_{y0}, \theta_{z0}$
. . .
$x_n, y_0, z_0, \theta_{x0}, \theta_{y0}, \theta_{z0}$
$x_0, y_1, z_0, \theta_{x0}, \theta_{y0}, \theta_{z0}$
$x_0, y_2, z_0, \theta_{x0}, \theta_{y0}, \theta_{z0}$
. . .
$x_0, y_n, z_0, \theta_{x0}, \theta_{y0}, \theta_{z0}$
$x_0, y_0, z_1, \theta_{x0}, \theta_{y0}, \theta_{z0}$
$x_0, y_0, z_2, \theta_{x0}, \theta_{y0}, \theta_{z0}$
. . .
$x_0, y_0, z_n, \theta_{x0}, \theta_{y0}, \theta_{z0}$
$x_0, y_0, z_0, \theta_{x0}, \theta_{y1}, \theta_{z0}$
$x_0, y_0, z_0, \theta_{x0}, \theta_{y2}, \theta_{z0}$
. . .
$x_0, y_0, z_0, \theta_{x0}, \theta_{yn}, \theta_{z0}$ TABLE 1-continued Sets of Transform Parameters
$(x, y, z, \theta_x, \theta_y, \theta_z)$ $x_0, y_0, z_0, \theta_{x0}, \theta_{y0}, \theta_{z1}$
$x_0, y_0, z_0, \theta_{x0}, \theta_{y0}, \theta_{z2}$
...
$x_0, y_0, z_0, \theta_{x0}, \theta_{y0}, \theta_{zn}$
...
$x_n, y_n, z_n, \theta_{xn}, \theta_{yn}, \theta_{zn}$ The processor 140 may be configured to carry out image registration between the 3-D CT image from the CT image forming unit 110 and the 3-D ultrasound image from the ultrasound image forming unit 120 to thereby form a 3-D ultrasound-CT registered image. The processor 140 may be further configured to extract a 2-D CT image corresponding to the 2-D ultrasound image from the 3-D ultrasound-CT registered image.

Figure 3:
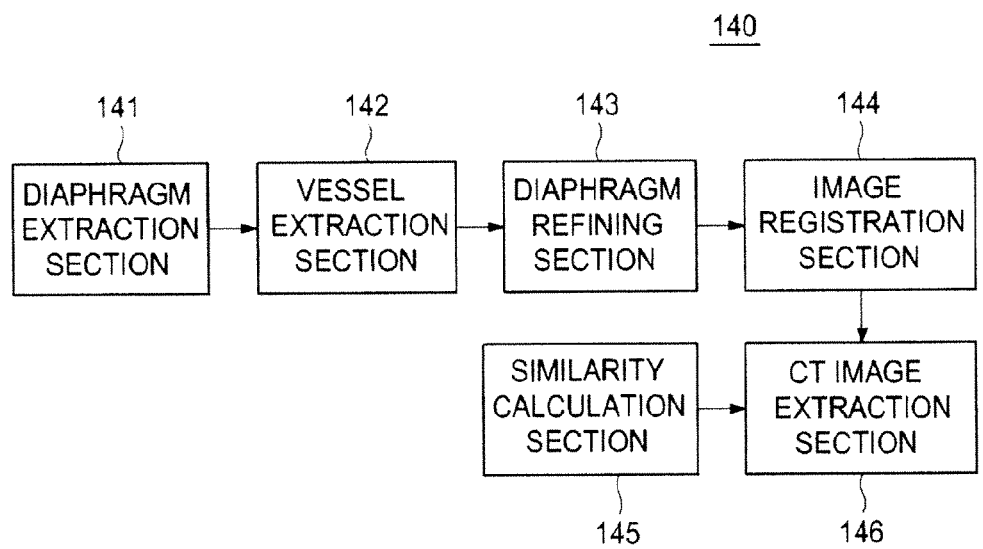
FIG. 3 is an embodiment illustrating a schematic diagram of a processor in accordance with the present disclosure.

As depicted in FIG. 3, there is shown an embodiment illustrating a schematic diagram of the processor 140 in accordance with the present disclosure. In an exemplary embodiment, the processor 140 may be configured to include a diaphragm extraction section 141, a vessel extraction section 142, a diaphragm refining section 143, an image registration section 144, a similarity calculation section 145 and a CT image extraction section 146.

The diaphragm extraction section 141 may be configured to extract a diaphragm from the 3-D ultrasound image received from the ultrasound image forming unit 120. Also, the diaphragm extraction section 141 may be configured to extract the diaphragm from the 3-D CT image received from the CT image forming unit 110. In an exemplary embodiment, the diaphragm extraction section 141 may be operable to perform a Hessian matrix based flatness test upon the respective 3-dimensional ultrasound and CT images to extract the diaphragm. The diaphragm may be considered as a curved surface in the respective 3-D ultrasound and CT images. Thus, regions, in which a voxel intensity change in a normal direction at a surface is greater than a voxel intensity change in a horizontal direction at the surface, may be extracted as the diaphragm.

In particular, the diaphragm extraction section 141 may select voxels having a relatively higher flatness than a reference flatness in order to extract the diaphragm. The voxels may be represented with pixels and the flatness $\mu(v)$ may be defined as the following equation (1).

$$\mu(v) = \phi_1(v)\phi_2(v)\phi_3(v)/\phi_{3_{max}}(v) \quad (1)$$

Figure 4:
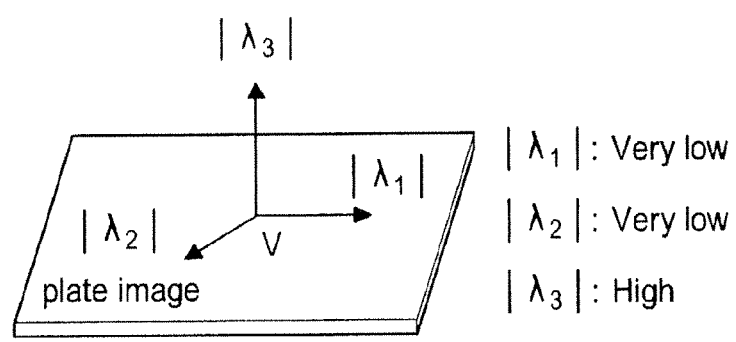
FIG. 4 is a schematic diagram illustrating an example of eigenvalues in the Hessian matrix.

$\phi_1(v)$, $\phi_2(v)$ and $\phi_3(v)$ in the equation (1) may be represented as the following equation (2).

$$\phi_1(v) = \left(1 - \frac{\lambda_1(v)}{\lambda_3(v)}\right)^2, \phi_2(v) = \left(1 - \frac{\lambda_2(v)}{\lambda_3(v)}\right)^2, \phi_3(v) = \sum_i \lambda_i(v)^2 \quad (2)$$

wherein $\lambda_1$, $\lambda_2$, and $\lambda_3$ denote eigenvalues of the Hessian matrix at voxel v. An example of the eigenvalues $\lambda_1$, $\lambda_2$, and $\lambda_3$ is illustrated in FIG. 4. The flatness $\mu(v)$ may be normalized to have values ranging from 0 to 1. A flatness map may be created based on the flatness obtained from all of the voxels according to the equations (1) and (2). Thereafter, the voxels having a relatively high flatness are selected. In an exemplary embodiment, the diaphragm extraction section 141 may be operable to select the voxels having the flatness over 0.1.

The diaphragm extraction section 141 may further perform morphological opening (i.e., morphological filtering) upon the selected voxels to remove small clutters therefrom. The morphological opening may be carried out by sequentially performing erosion and dilation. In particular, morphological boundaries in which the voxel values exist are removed as many as a predetermined number of the voxels and then contracted (erosion). Thereafter, the morphological boundaries are expanded as many as the predetermined number of the voxels. In an exemplary embodiment, the diaphragm extraction section 141 may contract and expand the morphological boundaries by 1 voxel.

The diaphragm is the largest surface in the respective 3-D ultrasound and CT images. The largest surface may be selected among candidates surfaces obtained by intensity-based connected component analysis (CCA) for the voxels and the selected surface may be regarded as the diaphragm. Voxel-based CCA is one of the methods of grouping regions in which voxel values exist. For example, it may be possible to compute the number of voxels connected to each of the voxels through a connectivity test by referring to values of voxels neighboring to the corresponding voxel (e.g., 26 voxels). The voxels, of which connected voxels are greater than the predetermined number, are selected as candidate groups. Since the diaphragm is the widest curved surface in the ROI of the respective 3-D ultrasound and CT images, the candidate group having the most connected voxels may be selected as the diaphragm. Thereafter, the surface of the diaphragm may be smoothened.

In another exemplary embodiment, while extracting the diaphragm from the 3-dimensional ultrasound image as described above, the diaphragm extraction section 141 may be operable to extract the diaphragm from the 3-D CT image, in response to input data from the user input unit (not shown), by using a commercial program or an extraction method, e.g., a seeded region growing segmentation method. The input data may include data for establishing a region of the diaphragm on the 3-D CT image and extracting the region therefrom.

The vessel extraction section 142 may be configured to perform vessel extraction upon the 3-D ultrasound and CT images sequentially through ROI masking, vessel segmentation and classification. In an exemplary embodiment, to avoid mis-extraction of vessels due to mirroring artifacts, the vessel extraction section 142 may be operable to perform the ROI masking upon the 3-D ultrasound and CT images by modeling the diaphragm to a polynomial curved surface. In such a case, the ROI masking, which models the diaphragm to the polynomial curved surface by using the least means square, may be used.

However, in case all of the lower portions of the modeled polynomial curved surface are eliminated, effective vessel information may be lost at some portion due to an error of the polynomial curved surface. In order to avoid losing the effective vessel information, the lower portion of the modeled polynomial curved surface may be eliminated in a marginal distance. For example, the marginal distance may be set to about 10 voxels at the lower portion of the ROI mask.

Subsequently, the vessel extraction section 142 may be further operable to segment a vessel region and a non-vessel region. In order to exclude non-vessel high intensity regions such as the diaphragm and vessel walls, the vessel extraction section 142 may estimate a low intensity boundary having a less reference boundary value in the ROI masked image. Thereafter, the vessel extraction section 142 may remove voxels with a higher intensity value than the reference boundary value. In an exemplary embodiment, an adaptive threshold scheme may be applied to the remaining regions for binarization thereof. The binarized segments may be labeled as vessel candidates.

Next, the vessel extraction section 142 may be further operable to remove non-vessel-type clutters from the binarization image to classify real vessels from the vessel candidates. In an exemplary embodiment, the vessel classification may include a size test for filtering out tiny background clutters, a structure-based vessel test, which evaluates the quality of fit to a cylindrical tube, for removing non-vessel type clutters (i.e., an initial vessel test), gradient magnitude analysis, and a final vessel test for perfectly removing the clutters from the binarization image. Although some clutters are not perfectly removed through the structure-based vessel test, an initial threshold may be marginally set so that all vessels may be included. For example, the initial threshold may be set to 0.6. At the final vessel test, clutters, which may be formed by small shading artifacts having low gradient magnitudes, may be perfectly removed in consideration with the variation of voxel values, i.e., gradient magnitudes, to thereby extract vessel data. In an exemplary embodiment, a threshold of the final vessel test may be set to 0.4.

In another exemplary embodiment, while extracting the vessel from the 3-dimensional ultrasound image as described above, the vessel extraction section 142 may be further operable to perform the vessel extraction upon the 3-D CT image, in response to input data from the user input unit. The input data may include data for establishing a region of the vessel on the 3-D CT image. In particular, the vessel extraction section 142 may set pixels having pixel values between a first threshold (T1) and a second threshold (T2) to have a value of 255 and the remaining pixels to have zero, by using pixel characteristics that the region of the vessel has a higher intensity than the remaining regions in the 3-D CT image. This process may be referred to as an intensity thresholding using two thresholds. As a result of such process, other regions having pixel values with higher intensities representing ribs and kidneys may be displayed as well as the vessel, i.e., the ROI. In order to eliminate the other regions rather than the vessel, connectivity of the vessel may be employed. In general, the vessel in a liver is comprised of a portal vein and a hepatic vein. The vessel extraction section 142 may be operable to establish two specific points corresponding to the portal vein and the hepatic vein as seed points and perform the seed region growing method using the seed points as starting points to thereby extract the vessel.

The diaphragm refining section 143 may be configured to perform refinement upon the diaphragm extracted in the 3-D ultrasound image by using the resultant vessel extracted from the vessel extraction section 142. In particular, the diaphragm refining section 142 may be operable to refine the diaphragm extracted from the 3-D ultrasound image by eliminating clutters by means of the resultant vessel. The clutters on the diaphragm extracted may be mainly placed near or on vessel walls. Especially, the vessel wall of an inferior vena cava (IVC) is likely to be connected to the diaphragm and cause clutters. These clutters may degrade the accuracy of feature based image registration so that the diaphragm should be refined. To refine the diaphragm, the vessel region is extracted according to the vessel extraction as described above, the extracted vessel region may be dilated, and then the dilated vessel region may be subtracted from the initially extracted diaphragm region to estimate vessel walls. The estimated vessel walls may be removed from the diaphragm region by performing the CCA and the size test once again.

The image registration section 144 may be configured to perform image registration between the 3-D ultrasound and CT images. The image registration section 144 may be operable to extract sample points corresponding to the vessel region and the diaphragm region, respectively, among the features extracted from the respective 3-D ultrasound and CT images In an exemplary embodiment, iterative closest point (ICP) based image registration may be performed with the sample points extracted from the respective 3-D ultrasound and CT images to thereby form a 3-D ultrasound-CT registered image.

The similarity calculation section 145 may be configured to calculate the similarity between the 2-D and 3-D ultrasound images while performing the rigid-body transform upon the 3-D ultrasound image. The operation of the similarity calculation section 145 will be described in detail hereinafter with reference to FIG. 5. The CT image extraction section 146 may be configured to extract a 2-D CT image corresponding to the 2-D ultrasound image from the 3-D ultrasound-CT registered image by means of the calculated similarity from the similarity calculation section 145.

Referring back to FIG. 1, the display unit 150 may be configured to display the 2-D ultrasound image related to the ROI and the 2-D CT image corresponding thereto. For example, the 2-D ultrasound image and the 2-D CT image may be superimposed over one another on the display unit 150. Alternatively, the 2-D ultrasound image and the 2-D CT image may be displayed on the display unit 150 in transverse or horizontal direction.

Hereinafter, operations for providing the 2-D CT image corresponding to the 2-dimensional ultrasound image from the 3-D ultrasound-CT registered image in accordance with an exemplary embodiment of the present disclosure will be described in detail with reference to FIGS. 5 to 7.

Figure 5:
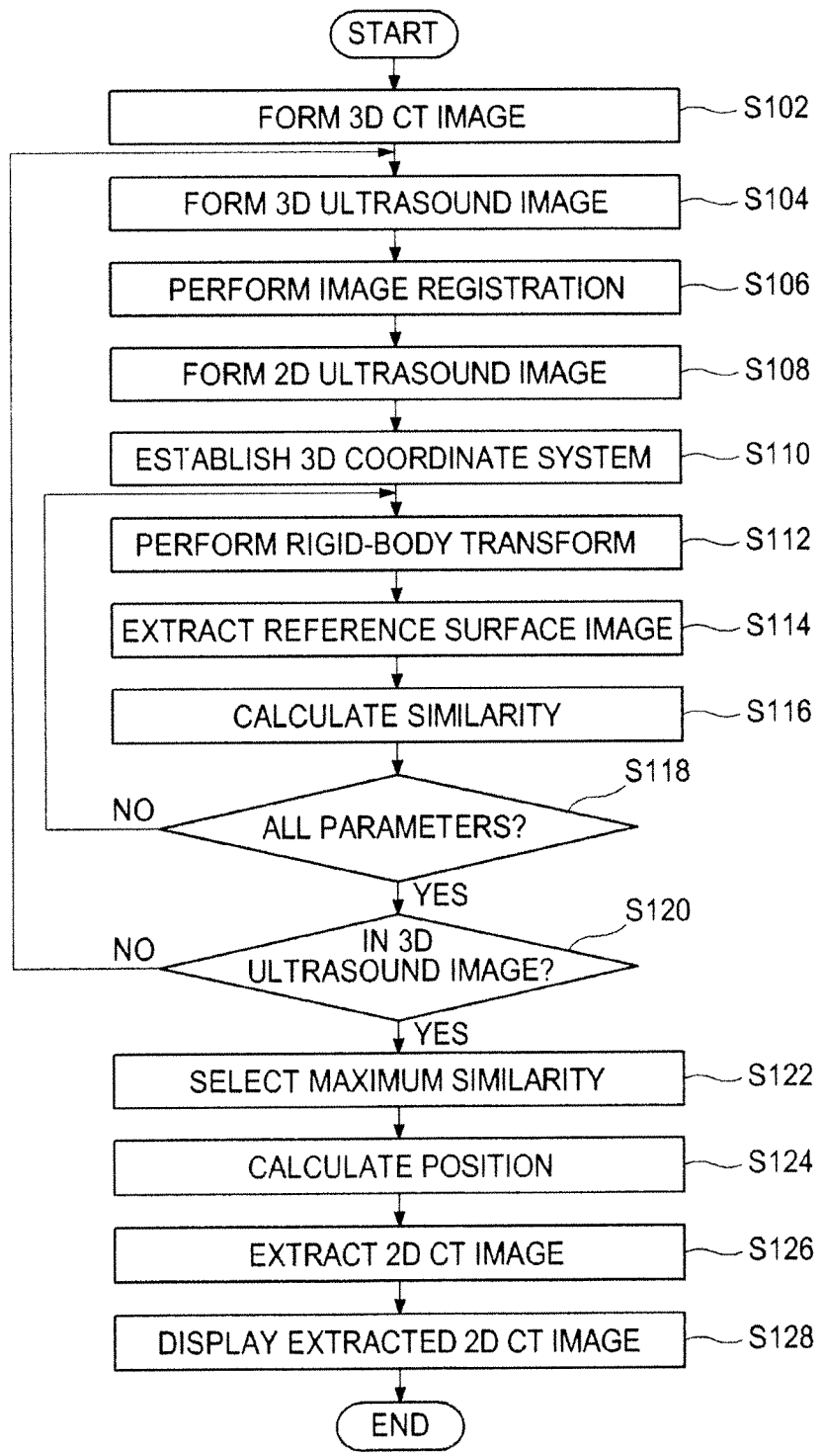
FIG. 5 is an embodiment illustrating a flowchart of a procedure for extracting a 2-D CT image corresponding to a 2-D ultrasound image from a 3-D ultrasound-CT registered image in accordance with the present disclosure.

Referring firstly to FIG. 5, the CT image forming unit 110 may be operable to form the 3-D CT image of the target object, at S102. The ultrasound image forming unit 120 may be operable to transmit ultrasound signals to the target object and receive ultrasound echo signals reflected therefrom to thereby form the 3-D ultrasound image of the target object, at S104.

The processor 104 may be operable to carry out image registration between the 3-D CT image from the CT image forming unit 110 and the 3-D ultrasound image from the ultrasound image forming unit 120 to thereby calculate a relative position of the 3-D ultrasound image with respect to the 3-D CT image, at S106.

Figure 6:
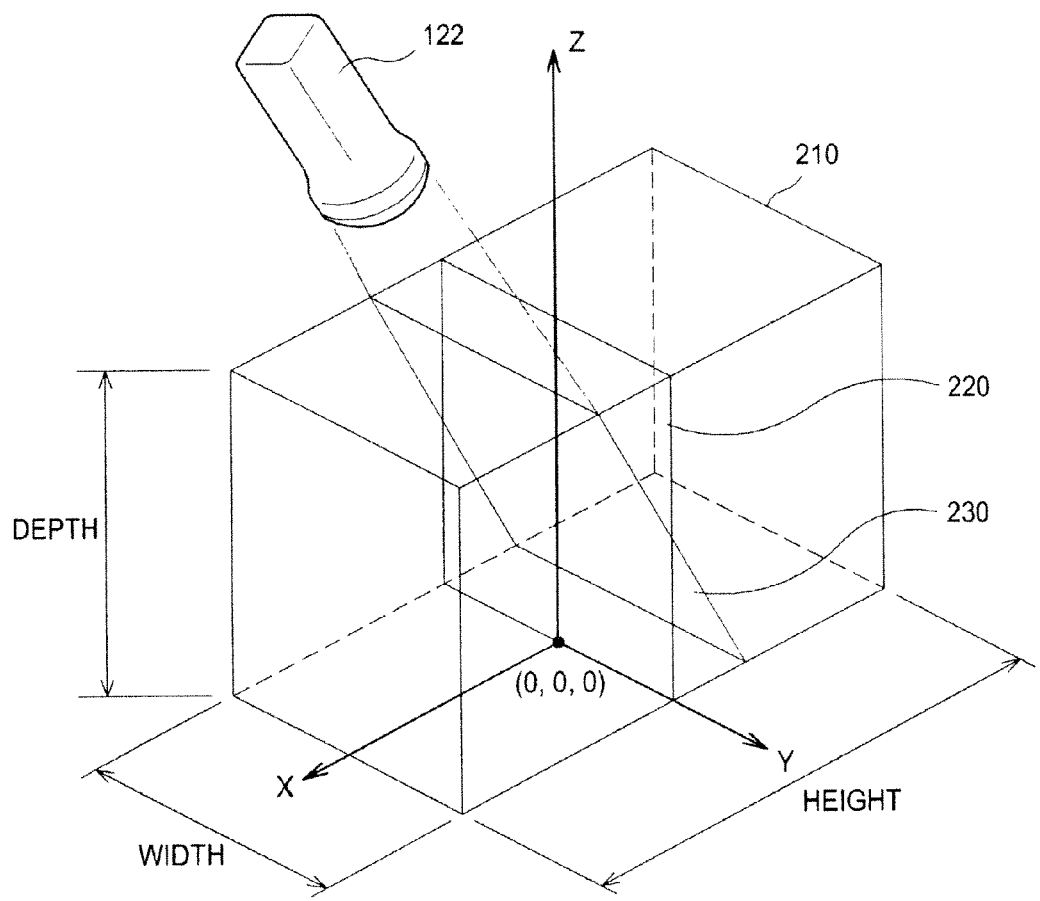
FIG. 6 is a schematic diagram illustrating examples of a 3-D ultrasound image, a 2-D ultrasound image, a 3-D coordinate system and a reference surface in accordance with the present disclosure.

The ultrasound image forming unit 120 may be operable to transmit ultrasound signals to the target object and receive ultrasound echo signals reflected therefrom to thereby form the 2-D ultrasound image 230 shown in FIG. 6 related to the ROI of the target object, at S108.

The similarity calculation section 145 of the processor 140 may be operable to establish the 3-D coordinate system with a reference surface 220 being set thereon in a 3-dimensional ultrasound image 210 as shown in FIG. 6, at S110. As depicted in FIG. 6, the reference surface 220 represents a cross-sectional surface that is fixed at predetermined coordinates on the 3-D rectangular coordinate system. Therefore, the reference surface has a non-variable position on the 3-D rectangular coordinate system irrespective of translation and/or rotation of the 3-D ultrasound image.

Figure 7:
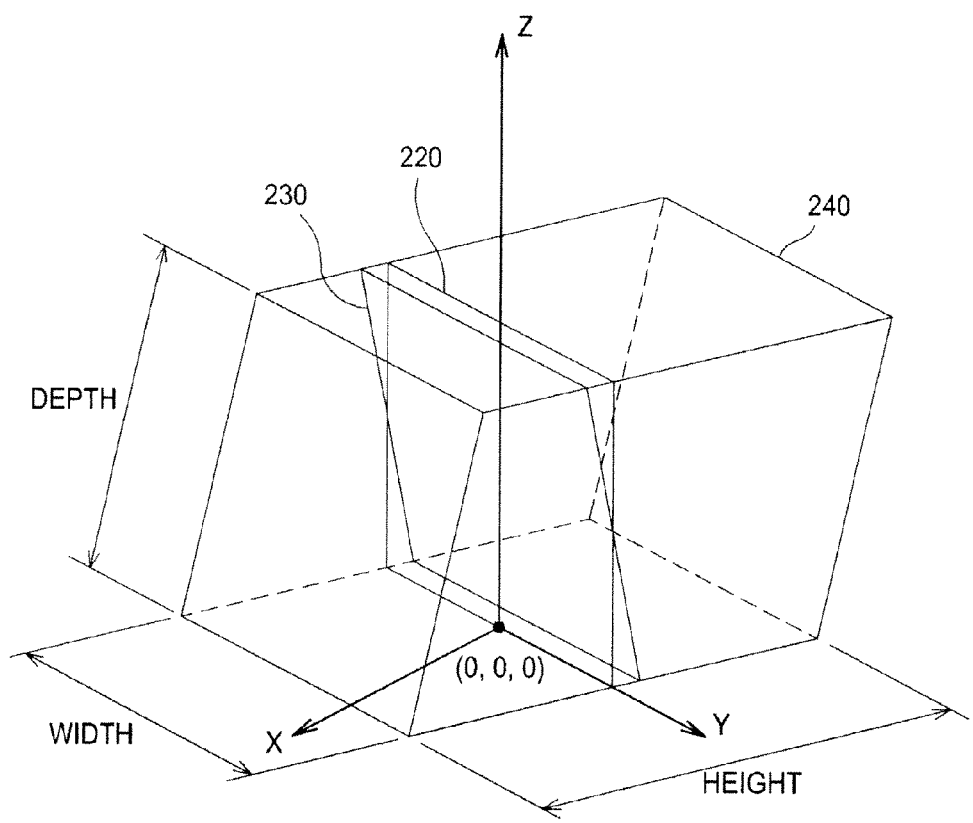
FIG. 7 is a schematic diagram illustrating an example of a 3-D rigid-body transformed ultrasound image in accordance with the present disclosure.

The similarity calculation section 145 of the processor 140 may be operable to retrieve sets of transform parameters shown in Table 1 from the storing unit 130 and then perform a rigid-body transform upon the 3-D ultrasound image 210 shown in FIG. 6 based on the retrieved sets of transform parameters to thereby form a 3-D rigid-body transformed ultrasound image 240 shown in FIG. 7, at S112. The similarity calculation section 145 may be operable to extract a reference surface image corresponding to the reference surface 220 from the 3-D rigid-body transformed ultrasound image 240, at S114. Herein, the reference surface images may be extracted from the 3-D rigid-body transformed ultrasound image 240, wherein each of the reference surface images is produced at every rigid-body transform when the sets of transform parameters are applied thereto.

Next, the similarity calculation section 145 may be operable to calculate similarities between the 2-D ultrasound image 230 and the extracted reference surface images, at S116. The similarity may be calculated through cross correlation, mutual information and the sum of squared intensity difference (SSID). In an exemplary embodiment, the similarity calculation section 145 may be operable to normalize the calculated similarities to have a value ranging from 0 to 2 by using normalized mutual information.

The similarity calculation section 145 may be operable to determine whether or not the rigid-body transform is carried out upon the 3-D ultrasound image 210 by applying all of the sets of transform parameters stored in the storing unit 130, at S118. In case all of the sets of transform parameters are not applied to the rigid-body transform, the similarity calculation section 145 may be operable to iteratively perform the above-mentioned procedures (i.e., from S112 to S116), until all of the sets of transform parameters are applied.

If all of the sets of transform parameters are applied to the rigid-body transform, the similarity calculation section 145 may then be operable to compare the respective calculated similarities with a predetermined threshold to thereby determine whether or not at least one among the calculated similarities is greater than the predetermined threshold, at S120. That is, through the above-mentioned comparison, the similarity calculation section 145 determines whether or not the 2-D ultrasound image exists in the 3-D rigid-body transformed ultrasound image.

If at least one among the calculated similarities is greater than the threshold similarity, the similarity calculation section 145 may be operable to select a maximum similarity out of the calculated similarities that are greater than the threshold similarity, at S122. In case none of the calculated similarities is greater than the threshold similarity, the similarity calculation section 145 may be operable to iteratively perform the above-mentioned procedures (i.e., from S104 to S118), until at least one calculated similarity is greater than the threshold similarity.

Next, the similarity calculation section 145 may be operable to calculate a position of the 2-D ultrasound image 230 within the 3-D rigid-body transformed ultrasound image 240 based on the set of transform parameters applied to the rigid-body transform that creates the selected maximum similarity, at S124. For example, the similarity calculation section 145 may be operable to calculate a position of the 2-D ultrasound image 230 within the 3-D rigid-body transformed ultrasound image 240 by using the set of transformation parameters (e.g., $(x_0, y_1, z_0, \theta_{x0}, \theta_{y0}, \theta_{z0})$) corresponding to the selected maximum similarity. In such case, the calculated position of the 2-dimensional ultrasound image 230 may be represented as a function of the inverse of the set of transformation parameters, e.g., $(-x_0, -y_1, -z_0, -\theta_{x0}, -\theta_{y0}, -\theta_{z0})$).

Thereafter, the CT image extraction section 146 of the processor 140 may be operable to extract a 2-D CT image corresponding to the 2-D ultrasound image the 3-D ultrasound-CT registered image based on the calculated position of the 2-dimensional ultrasound image and the relative position of the 3-D ultrasound image, at S126. Then, the display unit 150 may be operable to simultaneously display the extracted 2-D CT image and the 2-D ultrasound image, at S128. As described above, the extracted 2-D CT image and the 2-D ultrasound image may be superimposed over one another on the display unit 150, or displayed in transverse or horizontal direction.

Although exemplary embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of performing imaging, comprising:
    forming a 3-dimensional (3-D) CT image of a target object;
    forming a 3-dimensional (3-D) ultrasound image of the target object;
    storing sets of transform parameters for performing a rigid-body transform upon the 3-D ultrasound image;
    performing an image registration between the 3-D ultrasound image and the 3-D CT image to register a 3-D ultrasound-CT image;
    forming a 2-D ultrasound image related to a region of interest (ROI) of the target object;
    establishing a 3-D coordinate system with a reference surface being set thereon in the 3-D ultrasound image;
    performing a rigid-body transform upon the 3-D ultrasound image by sequentially applying the sets of transform parameters and calculating similarities between reference surface images and the 2-D ultrasound image, wherein each of the reference surface images is obtained every rigid-body transform when the sets of transform parameters are sequentially applied thereto and each of the reference surface images corresponds to the reference surface;
    extracting a 2-D CT image corresponding to the 2-D ultrasound image from the registered 3-D ultrasound-CT image based on the calculated similarities; and
    displaying the 2-D ultrasound and the extracted 2-D CT images.

2. The method of claim 1, wherein the target object includes a liver.

3. The method of claim 1, wherein performing the image registration further includes:
    extracting a diaphragm from the respective 3-D ultrasound and CT images by selecting a largest surface among candidate surfaces that are obtained from voxels;
    extracting a vessel from the respective 3-D ultrasound and CT images by selecting vessel candidates by removing voxels with a higher intensity value than a reference boundary value;
    removing clutters from the diaphragm extracted from the 3-D ultrasound image based on the vessel to refine the diaphragm;
    extracting sample points at the diaphragm and the vessel extracted from the respective 3-D ultrasound and CT images; and
    performing the image registration between the 3-D ultrasound and CT images based on the extracted sample points to calculate a relative position of the 3-D ultrasound image with respect to the 3-D CT image.

4. The method of claim 3, wherein extracting the diaphragm further includes:
 obtaining a flatness from voxels of the respective 3-D ultrasound and CT images with a flatness map;
 selecting voxels having a flatness greater than a reference value;
 performing a morphological filtering upon the selected voxels, eliminating morphological boundaries as many as a predetermined number of voxels, and contracting and expanding the morphological boundaries as many as the predetermined number of voxels to remove the clutters, wherein voxel values exist in the morphological boundaries;
 obtaining the candidate surfaces from the clutter-removed voxels through an intensity-based connected component analysis (CCA); and
 selecting the largest surface among the candidate surfaces to extract the diaphragm from the respective 3-D ultrasound and CT images.

5. The method of claim 3, wherein extracting the vessel further includes:
 modeling the diaphragm to a polynomial curved surface by performing an ROI masking upon the 3-D ultrasound and CT images;
 selecting the vessel candidates by removing voxels with the higher intensity value than the reference boundary value; and
 removing non-vessel-type clutters from the selected vessel candidates to extract the vessel as a resultant vessel,
 wherein the non-vessel-type clutters are removed through a structured-based vessel test, a gradient magnitude analysis and a final test.

6. The imaging method of claim 3, wherein further comprising receiving input data from a user before performing the image registration, wherein the input data includes first input data and second input data for establishing regions of the diaphragm and the vessel on the 3-D CT image, respectively.

7. The method of claim 6, wherein extracting the diaphragm further includes:
 extracting the diaphragm from the 3-dimensional CT image in response to the first input data from the user input section;
 obtaining the flatness from voxels of the 3-D ultrasound image with a flatness map;
 selecting voxels having a flatness greater than a reference value;
 performing a morphological filtering upon the selected voxels;
 eliminating the morphological boundaries as many as a predetermined number of the voxels;
 contracting and expanding the morphological boundaries as many as the predetermined number of the voxels;
 removing the clutters;
 obtaining the candidate surfaces from the clutter-removed voxels through an intensity-based connected component analysis (CCA); and
 selecting the largest surface among the candidate surfaces to extract the diaphragm from the 3-dimensional ultrasound image, wherein the voxel values exist in the morphological boundaries.

8. The method of claim 6, wherein extracting the vessel further includes:
 extracting the vessel from the 3-D CT image in response to the second input data from the user;
 extracting the vessel from the 3-D ultrasound image;
 modeling the diaphragm to a polynomial curved surface by performing an ROI masking upon the 3-D ultrasound image;
 selecting vessel candidates by removing voxels with a higher intensity value than a reference boundary value; and
 removing non-vessel-type clutters from the selected vessel candidates to extract the resultant vessel,
 wherein the non-vessel-type clutters are removed through a structured-based vessel test, a gradient magnitude analysis and a final test.

9. The method of claim 3, wherein performing the rigid-body transform and calculating the similarities further includes:
 retrieving the sets of transform parameters from a predetermined storing area;
 performing the rigid-body transform upon the 3-dimensional ultrasound image by sequentially applying the retrieved sets of transform parameters retrieved;
 extracting the reference images from the 3-D rigid-body transformed ultrasound images;
 calculating the similarities between the reference surface images and the 2-D ultrasound image;
 comparing each of the calculated similarities with a predetermined threshold;
 determining whether all of the sets of transform parameters are applied to the rigid-body transform or not;
 calculating the position of the 2-D ultrasound image based on the set of transform parameters applied to the rigid-body transform to produce a maximum similarity among the calculated similarities, when all of the sets of transform parameters are applied to the rigid-body transform and at least one of the calculated similarities is greater than the predetermined threshold; and
 extracting the 2-D CT image corresponding to the 2-D ultrasound image having the calculated position from the registered 3-D ultrasound-CT image based on the relative position,
 wherein the reference surface includes a cross-sectional surface fixed at predetermined coordinates on the 3-D coordinate system, and wherein the similarities are calculated through at least one of a cross correlation, mutual information and an sum of squared intensity difference (SSID).

10. The method of claim 9, wherein calculating the similarities further includes:
 forming a new 3-D ultrasound image of the target object, if none of the calculated similarities is greater than the predetermined threshold;
 performing an image registration between the new 3-D ultrasound image and the 3-D CT image;
 establishing the 3-D coordinate system with a reference surface being set thereon in the new 3-D ultrasound image;
 performing the rigid-body transform upon the new 3-D ultrasound image by sequentially applying the sets of transform parameters;
 calculating the similarities between the reference surface images and the 2-D ultrasound image;
 extracting a 2-D CT image corresponding to the 2-D ultrasound image from the registered 3-D ultrasound-CT image based on the calculated similarities; and
 displaying the 2-D ultrasound and CT images.

* * * * *